United States Patent [19]

Wijnberg et al.

[11] Patent Number: 4,814,477

[45] Date of Patent: Mar. 21, 1989

[54] DIOXAPHOSPHORINANES, THEIR PREPARATION AND USE FOR RESOLVING OPTICALLY ACTIVE COMPOUNDS

[75] Inventors: Hans Wijnberg, Haren; Wolter T. Hoeve, Groningen, both of Netherlands

[73] Assignee: Oce-Nederland B.V., Venlo, Netherlands

[21] Appl. No.: 65,121

[22] Filed: Jun. 19, 1987

Related U.S. Application Data

[63] Continuation of Ser. No. 785,837, Oct. 9, 1985, abandoned.

[30] Foreign Application Priority Data

Oct. 24, 1984 [NL] Netherlands ............................ 8403224

[51] Int. Cl.$^4$ .......................... C07F 9/21; C07B 57/00
[52] U.S. Cl. ...................................... 658/86; 562/401; 564/303; 564/304
[58] Field of Search ................... 558/86, 146; 562/401; 564/303, 304

[56] References Cited

FOREIGN PATENT DOCUMENTS 180276 5/1986 European Pat. Off. .............. 558/86

OTHER PUBLICATIONS

Kainosho et al., "Bull. of the Chemical Society of Japan," vol. 42, (1969) pp. 1713–1717.
Matrosov et al., "Chem. Abst.", vol. 85, (1976) 85:20188a.
Cram et al., "Organic Chemistry," (1964) Second Editions, pp. 162–175.
Majoral et al., "Chem Abst.," vol. 69, (1968) 26898y.

Primary Examiner—Anton H. Sutto
Attorney, Agent, or Firm—Reed, Smith, Shaw & McClay

[57] ABSTRACT

A new family of compounds known as dioxaphosphorinanes having the formula:

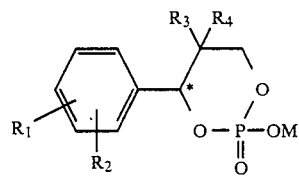

wherein, M represents a hydrogen atom, a metal ion or an ammonium ion; R1 and R2, individually, represents a hydrogen atom, a halogen atom, an alkyl group having from 1 to 4 carbon atoms, an alkoxy group having from 1 to 4 carbon atoms or a nitro group or, together, represent a methylene dioxy group; and R3 and R4, individually, represents a halogen atom, an alkyl group having from 1 to 4 carbon atoms or a hydrogen atom so long as only one of the groups R3 and R4 represents a hydrogen atom or, together, represent a cyclohexyl group.

A method for preparing these dioxaphosphorinanes by reacting phosphoryl chloride with a substituted 1-phenyl-1,3-dihydroxypropane is described. Also described is a method for resolving the new dioxaphosphorinanes into their optical isomers by reacting them with an optically active amino-compound. Similarly, a method for resolving the racemates of several amino-compounds, such as hydroxyphenylglycine and phenylalanine, into optically active isomers by reacting with a dioxaphosphorinane is described.

20 Claims, No Drawings

DIOXAPHOSPHORINANES, THEIR PREPARATION AND USE FOR RESOLVING OPTICALLY ACTIVE COMPOUNDS

This is a continuation of co-pending application Ser. No. 785,387 filed on 10/9/85, now abandoned.

BACKGROUND OF THE INVENTION

1. Field of the Invention

The present invention relates to optically active compounds, their preparation and their use for resolving racemates of optically active amino-compounds into individual optical isomers.

2. Description of the Prior Art

Several optically active acids are known which can be used as resolving agents for racemates of optically active amino-compounds, including amino-acids, which are used as intermediates for the preparation of pharmaceuticals. U.S. Pat. No. 3,848,030 describes such optically active acids. More particularly, the optically active acids disclosed in this patent are symmetrical around the acid group. Conversely, optically active amino-compounds can be used for separating specific racemates of optically active acids. Some examples of optically active amino-compounds are phenylglycine, para-hydroxyphenylglycine, 2-amino-1-butanol and 2-amino-1-phenyl-1,3-propanediol.

Optically active acids, however, are expensive and, typically, are prepared by a complex process. Moreover, these optically active resolving agents are not always resistant to racemization in an acidic or alkaline medium and they are often difficult to recover after use. Also, they generally are suitable only for separating a small number of racemates of optically active amino-compounds. For these reasons, attempts are continually being made to develop optically active acids without the above disadvantages.

SUMMARY OF THE INVENTION

Generally, the present invention provides new optically active acids known as dioxaphosphorinanes having the general formula:

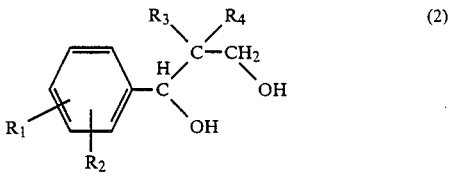

wherein, M represents a hydrogen atom, a metal ion or an ammonium ion; R1 and R2, individually, represents a hydrogen atom, a halogen atom, an alkyl group having from 1 to 4 carbon atoms, an alkoxy group having from 1 to 4 carbon atoms or a nitro group or, together, represent a methylene dioxy group; and R3 and R4, individually, represents a halogen atom, an alkyl group having from 1 to 4 carbon atoms or a hydrogen atom so long as only one of the groups R3 and R4 represents a hydrogen atom or, together, represent a cyclohexyl group.

The compounds of formula (1) are simple and cheap to prepare, are easily resolved into optical isomers, are very resistant to racemization in an alkaline or acidic medium and are also easy to recover. These compounds also have the advantage of both isomers, the (+) and the (−) form, being available. This in contrast to the optically active compounds derived from natural products of which generally only one of the isomers is available.

DESCRIPTION OF THE PREFERRED EMBODIMENTS

The present invention particularly provides dioxaphosphorinanes of formula (1) in which M is a hydrogen atom; R1 and R2, individually, represent a hydrogen atom, a chlorine atom, a methyl group, an ethyl group, a methoxy group, an ethoxy group or a nitro group or, together, represent a 3,4-methylene dioxy group; and R3 and R4, individually, represent a hydrogen atom, a chlorine atom, a methyl group or, together, represent a cyclohexyl group. Examples of suitable compounds, according to formula (1), are given in Table 1.

The *Bulletin of the Chemical Society of Japan,* Vol. 42 (June 1969) pp. 1713–18, discloses the chemical formula for seven 1,3,2-dioxaphosphorinanes but gives no indication that the isomers of these dioxaphosphorinanes are optically active or that they can be resolved.

Racemic dioxaphosphorinanes can be prepared by reacting a racemic diol, having the following general formula:

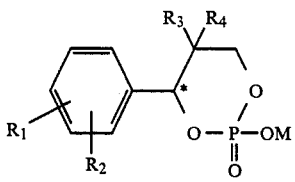

wherein, R1, R2, R3 and R4 have the same meanings as in formula (1), with phosphoryl chloride and hydrolyzing the resulting product in an alkaline medium.

The racemic diols of formula (2) are known to those skilled in the art and can be obtained in a known manner. In cases where R3 and R4 in formula (2) represent an alkyl group, such as methyl and ethyl, respectively, a mixed aldol condensation, for example, can be used by reacting one equivalent of an aromatic aldehyde with two equivalents of a dialkyl acetaldehyde in the presence of one equivalent of potassium hydroxide in alcoholic medium. This reaction results in an aldol which is reduced to a 1,3-diol by the excess dialkyl acetaldehyde. Such a reaction is described in U.S. Pat. No. 3,092,639.

In cases in which R3 and R4, respectively, denote a hydrogen and a halogen atom, the 1,3-diols can easily be prepared by reacting N-chlorosuccinic acid imide or bromine with 3-phenyl-allyl alcohol. These reactions are described in Dolby L. J., Wilkens C., Frey T. G., *Journal Org. Chem.,* Vol. 31 (1966) at p. 1110 and Bretschneider H., Karpitschka N., *Monatsch. Chem.,* Vol. 84 (1953) at p. 1043.

Optical isomers of the dioxaphosphorinanes can be separated from their corresponding racemate with optically active amino-compounds. Some optically active amino-compounds which can be used for this purpose are (−)-ephedrine, (+)-2-amino-1-phenyl-1,3 propanediol, (−)-2-amino-1-butanol and (−)-para-hydroxyphenylglycine. For each of the dioxaphosphorinanes in Table 1, the optically active amines that can be used to separate the relevant optically active isomers from one another are indicated.

Conversely, optically active isomers of the dioxaphosphorinanes can be used for separating the optically active isomers of various amino-compounds which are used as intermediates for the preparation of pharmaceutical products. Although it is not possible to separate the optical isomers of all amino-compounds with just a single dioxaphosphorinane, the dioxaphosphorinanes are fairly universally usable to obtain the isomers of amino-compounds.

For example, using 1,3,2-dioxaphosphorinane, 5,5-dimethyl-4-(2'-methoxyphenyl)-2-hydroxy-2-oxide (compound 3 in Table 1) it is possible to separate the optically active isomers of the following five amino-compounds: phenylalanine, S-(amino-iminomethyl)-β-mercaptobutyric acid, para-hydroxyphenylglycine, 1-phenyl-2-paramethoxyphenyl-ethylamine and N-[1-(4'-methoxy-phenyl)-isopropyl]-N-ethylamine.

Similarly, the 1,3,2-dioxaphosphorinane, 5,5-dimethyl-4-(2'-chlorophenyl)-2-hydroxy-2-oxide (compound 9 in Table 1) is suitable not only for resolving the five amino-compounds mentioned above into their optical isomers, but also for resolving 1,2,3,4-tetrahydro-5-methoxy-N-propyl-2-naphthalene-amine and 1,2-di-(4'-chlorophenyl)-1,2-diamino-ethane.

A third compound suitable for resolving para-hydroxyphenylglycine, which is very important for the preparation of pharmaceutical products, is 1,3,2-dioxaphosphorinane, 5,5-dimethyl-4-(2',4'-dichloro-phenyl)-2-hydroxy-2-oxide (compound 11 in Table 1). This dioxaphosphorinane has also been found very suitable for resolving 1,2-di(4'-chlorophenyl)-1,2-diamino-ethane and 1-phenyl-2-paramethoxyphenyl-ethylamine.

The universal usability of dioxaphosphorinanes as optical separators is further enhanced by the wide range of optically active dioxaphosphorinanes from which to choose.

heated with reflux for 4 hours and then concentrated by evaporation. A solution of 100 g. of sodium hydroxide (2.5 mole) in 1 liter of water was added to the resulting residue and was heated with agitation until a substantially clear liquid was obtained. The mixture, from which a granular substance rapidly separated, was cooled to 70° C. and mixed with 290 ml. of concentrated hydrochloric acid. An oil formed, which rapidly solidified. After filtering off the remaining liquid, washing with water and ether, followed by drying at 80° C., 201.6 g. (0.729 mole) of the above dioxaphosphorinane was obtained, representing a yield of 85%.

EXAMPLE 2

Preparation of 1,3,2-dioxaphosphorinane, 5,5-dimethyl-4-(2'-methoxyphenyl)-2-hydroxy-2-oxide (Compound 3 in Table 1).

A mixture of 122 g. (0.796 mole) of phosphoryl chloride in 250 ml. of dichloromethane was added over a period of 0.5 hour with cooling to 163.5 g. (0.779 mole) of 1-(2'-methoxyphenyl)-2,2-dimethyl-1,3-dihydroxy-propane and 168.7 g. (1.67 mole) of triethylamine in 350 ml. of dichloromethane. After heating for 4.5 hours with reflux, the reaction mixture was twice extracted with 750 ml. of water. The water layers were extracted with 300 ml. of dichloromethane.

All the dichloromethane fractions were dried on sodium sulphate and concentrated by evaporation. The remaining oil was heated with a solution of 88 g. (2.2 mole) of sodium hydroxide in 800 ml. of water until a clear solution formed. This solution was cooled and 250 ml. of concentrated hydrochloric acid was added at 40° C. The result was an oil which solidified on further

TABLE 1

| No. | R1 | R2 | R3 | R4 | Racemate Melting Point | Resolved Into Optical Isomers With (M = H) | Melting Point of Crystallized Optical Isomer | Absolute Rotation [A]578 of the Optically Pure Forms |
|---|---|---|---|---|---|---|---|---|
| 1 | H | H | $CH_3$ | $CH_3$ | 224–224.5 | B | 230–231 | 60.1 |
| 2 | 2-$NO_2$ | H | $CH_3$ | $CH_3$ | | D | 229.5–230.5 | 489 |
| 3 | 2-$OCH_3$ | H | $CH_3$ | $CH_3$ | 204–205 | A | 195–197 | 63.8 |
| 4 | 4-$OCH_3$ | H | $CH_3$ | $CH_3$ | 195–196.5 | A,B | 203.5–204.5 | 68.3 |
| 5 | 3,4-$OCH_2O$— | | $CH_3$ | $CH_3$ | 200–201.5 | A | 201 | 59.2 |
| 6 | 4-Cl | H | $CH_3$ | $CH_3$ | 222–223 | A,B,C | 217–218 | 59.5 |
| 7 | H | H | Cl | H | 174–178 | A,B | | |
| 8 | H | H | Br | H | 190–192.5 | A | | |
| 9 | 2-Cl | H | $CH_3$ | $CH_3$ | 221.5–225.5 | A,D | 225.5–227 | 49.3 |
| 10 | 2-$OC_2H_5$ | H | $CH_3$ | $CH_3$ | 194–195 | A,D | 215.5–216.5 | 60.9 |
| 11 | 2-Cl | 4-Cl | $CH_3$ | $CH_3$ | 212.5–213 | A,B | 238.5–240.5 | 46.6 |
| 12 | 2-Cl | 6-Cl | $CH_3$ | $CH_3$ | 212–213 | A | 256–258 | 36.8 |
| 13 | 3-$NO_2$ | H | $CH_3$ | $CH_3$ | 209–213 | A,D | 242–250 | 56.9 |
| 14 | 4-$CH_3$ | H | $CH_3$ | $CH_3$ | 219–221 | B | 220–222 | 66.9 |
| 15 | 2-Cl | H | cyclohexyl | | 224.5–225.5 | A,D | 246.5–247.5 | 29.5 |

A = (−)-ephedrine
B = (+)-2-amino-1-phenyl-1,3-propanediol
C = (−)-2-amino-1-butanol
D = (−)-para-hydroxyphenylglycine The present invention will be explained in detail by reference to the following examples.

EXAMPLE 1

Preparation of 1,3,2-dioxaphosphorinane, 5,5-dimethyl-4-(2'-chlorophenyl)-2-hydroxy-2-oxide (Compound 9 in Table 1).

A solution of 141.0 g. (0.92 mole) of phosphoryl chloride in 250 ml. of dichloromethane was added over a period of 1 hour with agitation to 183.1 g. (0.854 mole) of 1-(2'-chlorophenyl)-2,2-dimethyl-1,3-dihydroxy-propane in 400 ml. of dichloromethane. The mixture was cooling. After removal of the liquid, washing with water and ether, and drying, 173.3 g. (0.637 mole) of the above dioxaphosphorinane was obtained, representing a yield of 83%.

EXAMPLE 3

The compounds 1, 2, 6, 11, 12, 13 and 15 listed in Table 1 were prepared in the same way as described in Example 1 using each compound's corresponding diol.

EXAMPLE 4

The compounds 4, 5, 10 and 14 listed in Table 1 were prepared in the same way as described in Example 2 using each compound's corresponding diol.

EXAMPLE 5

Preparation of 1,3,2-dioxaphosphorinane, 5-bromo-4-phenyl-2-hydroxy-2-oxide (Compound 8 in Table 1).

A mixture of 18.5 g. (0.121 mole) of phosphoryl chloride and 50 ml. of dichloromethane was added over a period of 15 minutes to a mixture of 23.1 g. (0.100 mole) of 2-bromo-1-phenyl-1,3-propanediol, 18.1 g. (0.229 mole) of pyridine and 200 ml. of dichloromethane. The mixture was heated with reflux for 3 hours and washed twice with 250 ml. of water. The water layers were extracted with 150 ml. of dichloromethane. The dichloromethane fractions were dried on sodium sulphate and then concentrated by evaporation. The resulting residue was mixed with 12.5 g. (0.313 mole) of sodium hydroxide and 200 ml. of water and was heated for 1.5 hours at a temperature of 65° C. to 70° C. After cooling to 20° C., the resulting solution was acidified with 50 ml. of concentrated hydrochloric acid. The precipitate was sucked off and washed with water and ether giving 23.9 g. (81.6 m. mole) of the above dioxaphosphorinane, representing a yield of 82%.

EXAMPLE 6

Resolution of the optical isomers of 1,3,2-dioxaphosphorinane, 5,5-dimethyl-4-(2'-ethoxyphenyl)-2-hydroxy-2-oxide (Compound 10 in Table 1).

A mixture of 115.4 g. (0.403 mole) of the racemate of compound 10 in Table 1 and 68.0 g. (0.407 mole) of (−)-para-hydroxyphenylglycine was dissolved with heating in 1400 ml. of a 1:1 mixture of water and ethanol. The solution was cooled by leaving it at room temperature for 5 hours with agitation and the occasional addition of seed crystals. The diastereomeric salt which crystallized out was filtered off and washed with 250 ml. of water. After drying, the weight was 66.8 g. (0.147 mole) and the optical rotation $[\alpha]_{578} = -98.5$. The yield was 37%. The diastereomeric salt obtained in this way was agitated for 5 hours with a mixture of 30 ml. of concentrated hydrochloric acid and 300 ml. of water. After filtration and drying, 42.0 g. (0.147 mole) of dioxaphosphorinane with an optical rotation $[\alpha]_{578} = -60.9$ was obtained. Hydrolysis of the filtrate remaining after filtration of the diastereomeric salt, known as the main filtrate, yielded 61.6 g. of dioxaphosphorinane with an optical rotation $[\alpha]_{578} = +37.0$. $[\alpha]_{578}$ here and hereinafter is given for C=0.5 g. per 100 ml. solution in methanol unless otherwise stated.

EXAMPLE 7

Resolution of the optical isomers of 1,3,2-dioxaphosphorinane, 5,5-dimethyl-4-phenyl-2-hydroxy-2-oxide (Compound 1 in Table 1).

A mixture of 24.2 g. (0.1 mole) of the racemate of compound 1 in Table 1 and 16.7 g. (0.1 mole) of (+)-2-amino-1-phenyl-1,3-propanediol was dissolved by heating in 200 ml. of ethanol. The solution was concentrated by evaporation and 11.9 g. of diastereomeric salt was obtained therefrom after cooling. The filtrate was further concentrated by evaporation and combined with a mixture of 122 g. (0.504 mole) of the racemate of compound 1, 85 g. (0.509 mole) of (+)-2-amino-1-phenyl-1,3-propanediol and 450 ml. of ethanol. After heating until dissolution, the mixture was cooled by leaving it at room temperature for 12 hours with agitation. The precipitated salt was filtered off, washed with water and ether and dried. In this second step, 46.85 g. of diastereomeric salt with an optical rotation $[\alpha]_{578} = -15.7$ was obtained. Another 31.7 g. of diastereomeric salt with $[\alpha]_{578} = -11.2$ was crystallized out of the washing liquids, and the main filtrate after concentrating by evaporation and cooling to −15° C., and yielded 20.5 g. of pure diastereomatic salt by recrystallization with 80 ml. of ethanol. The total production of crystallized out diastereomeric salt was 79.26 g. (0.194 mole), representing a yield of 32%.

The 46.85 g. of diastereomeric salt from the second step were converted with a 100% yield into the free dioxaphosphorinane by treatment with 150 ml. of hydrochloric acid in 300 ml. of water. The optical rotation was $[\alpha]_{578} = -60.1$ (C=1, CH$_3$OH).

From the remaining filrate of the third step, it was possible after considerable concentration by evaporation to filter off a portion of salt which after hydrolysis, yielded 32.86 g. of dioxaphosphorinane with $[\alpha]_{578} = 37.0$.

After further concentration of the remaining filtrate, another portion of salt was obtained which, after hydrolysis, yielded 43.0 g. of dioxaphosphorinane with $[\alpha]_{578} = +42.9$. Recrystallization of the latter two portions from a 3:1 mixture of ethanol and water yielded 23.47 g. and 31.61 g., respectively, of purified dioxaphosphorinane with $[\alpha]_{578} = +54.2$ and 60.2, respectively.

EXAMPLE 8

Resolution of the optical isomers of 1,3,2-dioxaphosphorinane, 5,5-dimethyl-4-(2'4'-dichlorophenyl)-2-hydroxy-2-oxide (Compound 11 in Table 1).

A mixture of 285.5 g. (0.918 mole) of the above dioxaphosphorinane and 155 g. (0.939 mole) of (−)-ephedrine was dissolved with heating in 500 ml. of ethanol. The solution was cooled to 20° C. with agitation. Agitation was continued for another 4 hours and then the mixture was allowed to stand for 12 hours. After filtration of the precipitate, washing with ether, recrystallization from 430 ml. of ethanol and drying, 118.5 g (0.249 mole) of diastereomeric salt was obtained with an optical rotation $[\alpha]_{578} = +6.2$. The yield was 27%. Using 117 g. hydrolysis with 50 ml. of concentrated hydrochloric acid in 450 ml. of water gave 75.45 g. (0.243 mole of dioxaphosphorinane with an optical rotation $[\alpha]_{578} = +46.6$. The yield was 97%.

From the main filtrate, after evaporation of 250 ml. of ethanol, a diastereomeric salt was precipitated which, after filtration, washing with ether and drying, weighed 52.5 g. (0.110 mole) and had an optical rotation $[\alpha]_{578} = -44.0$. Hydrolysis of this product with 20 ml. of hydrochloric acid in 180 ml. of water yielded 32.4 g. (0.104 mole) of dioxaphosphorinane with $[\alpha]_{578} = -43.2$.

EXAMPLE 9

Resolution of the optical isomers of 1,3,2-dioxaphosphorinane, 5,5-dimethyl-4-(2'chlorophenyl)-2-hydroxy-2-oxide (Compound 9 in Table 1).

A mixture of 169.9 g. (0.615 mole) of the racemate of compound 9 in Table 1 and 102.7 g. (0.615 mole) of (−)-para-hydroxyphenylglycine was dissolved with heating in a mixture of 1030 ml. of 96% ethanol and 800 ml. of water. The mixture was cooled by leaving it at room temperature with agitation and the occasional addition of seed crystals. Agitation was then continued for 12 hours and the precipitated diastereomeric salt was filtered off, washed with 300 ml. of water and dried. The production was 103.6 g. (0.234 mole) and represented a 38% yield. The optical rotation was $[\alpha]_{578} = -95.7$.

The resulting diastereomeric salt was hydrolyzed by agitating it for 6 hours with 105 ml. of concentrated hydrochloric acid and 465 ml. of water. After filtration, washing with water and drying, 58.8 g. (91% yield) of the dioxaphosphorinane were obtained having an optical rotation of $[\alpha]_{578} = -49.3$.

The main filtrate after the treatment with para-hydroxyphenylglycine was allowed to stand for 2 days and then agitated for 7 hours with 150 ml. of concentrated hydrochloric acid. After suction filtration, washing and drying, 74.3 g. of dioxaphosphorinane was obtained with $[\alpha]_{578} = +48.9$.

EXAMPLE 10

Resolution of the optical isomers of 1,3,2-dioxaphosphorinane, 5,5-dimethyl-4-(2'-nitrophenyl)-2-hydroxy-2-oxide (Compound 2 in Table 1).

A mixture of 58.6 g. (0.204 mole) of the racemate of compound 2 in Table 1 and 34.2 g. (0.205 mole) of (−)-para-hydroxyphenylglycine was dissolved with heating in 600 ml. of a 1:1 mixture of water and absolute alcohol. The mixture was cooled by leaving it at room temperature with agitation and the occasional addition of seed crystals. After 12 hours of agitation, the precipitated diastereomeric salt was filtered off, washed with water and dried at 75° C. The production was 40.5 g. (89.2 mole) which represented a 44% yield. The optical rotation of the salt was $[\alpha]_{578} = -353$. 39.95 g. of the resulting salt was agitated for 7 hours with 45 ml. of concentrated hydrochloric acid in 135 ml. of water. The precipitate was filtered off, washed and dried giving 23.6 g. (82.8 m. mole) representing a 94% yield of dioxaphosphorinane having $[\alpha]_{578} = -463$.

The main filtrate after the treatment with para-hydroxyphenylglycine produced 27.7 g. of dioxaphosphorinane having an optical rotation $[\alpha]_{578} = +409$ after decomposition with hydrochloric acid. Recrystallization of this product with CH₃OH yielded 17.73 g. with $[\alpha]_{578} = +489$. Over 6 g. of the dioxaphosphorinane with positive rotation were additionally obtained after concentrating the filtrate by evaporation.

It was found that the resolutions according to Examples 6 to 10 are reversible. The optical isomers of the relevant amine can be separated by using the relevant dioxaphosphorinane.

EXAMPLE 11

Resolution of the optical isomers of phenylalanine with (−)-1,3,2-dioxaphosphorinane, 5,5-dimethyl-4-(2'-chlorophenyl)-2-hydroxy-2-oxide (Compound 9 in Table 1).

A mixture of 8.80 g. (31.8 m. mole) of the (−) form of the dioxaphosphorinane and 5.25 g. (31.8 m. mole) of the phenylalanine racemate was dissolved with heating in 60 ml. of water and 25 ml. of absolute alcohol. The mixture was cooled by leaving it at room temperature with agitation and the occasional addition of seed crystals. After 5.5 hours of agitation, the precipitate was filtered off, washed with water and dried. The production was 6.03 g. (13.7 m. mole), representing a 43% yield and having an optical rotation $[\alpha]_{578} = -26.6$. 5.87 g. (13.3 m. mole) of this product were hydrolyzed by agitation for 7 hours with 7 ml. of concentrated hydrochloric acid and 63 ml. of water. The dioxaphosphorinane reliberated in this way was filtered off and washed and after drying weighed 3.5 g. (12.7 m. mole) representing a 95% recovery. The filtrate was dissolved in a mixture of 10 ml. of water and 5 ml. of ethanol and neutralized with a dilute sodium hydroxide solution. The resulting precipitate consisted of 1.1 g. (+)-phenylalanine having an optical rotation $[\alpha]_{578} = +34.2$ (C=1.96, H₂O). The remaining filtrate after concentration by evaporation and purification over a Dowex −H+ column yielded another 0.75 g. phenylalanine having $[\alpha]_{578} = +32.8$. The total production was 1.85 g. (11.2 m. mole) representing an 84% yield.

EXAMPLE 12

Resolution of the optical isomers of 1-phenyl-2-paramethoxyphenylethylamine with (+)-1,3,2-dioxaphosphorinane, 5,5-dimethyl-4-(2'-4'-dichlorophenyl)-2-hydroxy-2-oxide (Compound 11 in Table 1).

A mixture of 12.5 g. of the impure amine and 14.5 g. (46.6 m. mole) of the dioxaphosphorinane was heated with 105 ml. of methanol for 60 hours with agitation. From the mixture, it was possible to recover 8.14 g. (15.1 m. mole) of the diastereomeric salt representing a 32% yield and having an optical rotation $[\alpha]_{578} = +76.9$. 7.93 g. of this product were agitated with 150 ml. of 1N sodium hydroxide solution. After agitating the suspension for 16 hours, 50 ml. of chloroform were added and after agitation for another 0.5 hour the solid was filtered. From this solid, which consisted of the sodium salt of the dioxaphosphorinane, the free acid was recovered by acidification. The filtrate, which consisted of two layers, was separated by means of a separating funnel. The aqueous layer was extracted with 40 ml. of chloroform and the chloroform layer was washed with water. The chloroform fractions were dried, concentrated by evaporation and purified by Kugelrohr distillation at 135° C. under a pressure of 0.03 mm. Hg. The production was 3.05 g. (13.4 m. mole) of a colorless amine representing a yield of 91% and having an optical rotation $[\alpha]_{578} = +64.3$ (C=1.07, CH₃OH).

EXAMPLE 13

Resolution of the optical isomers of the amine of Example 12 with (−)-1,3,2-dioxaphosphorinane 5,5-dimethyl-4-(2'-methoxyphenyl)-2-hydroxy-2oxide (Compound 3 in Table 1).

A mixture of 16.8 g. (61.8 m. mole) of the dioxaphosphorinane and 15.5 g. of the impure amine was dissolved with heating in a mixture of 50 ml. of 96% ethanol and 10 ml. of water. After cooling and allowing the mixture to stand for 12 hours with agitation, it was possible to filter off 7.92 g. (15.9 m. mole) of diastereomeric salt having an optical rotation $[\alpha]_{578} = -86.3$. This represented a yield of 26%. 7.5 g. of this product was agitated for 5 hours with a solution of 4.0 g. of sodium hydroxide in 100 ml. of water. The liquid was extracted twice with 50 ml. of chloroform, washed with 50 ml. of water, dried and concentrated by evaporation. Kugelrohr distillation produced 3.2 g. (14.1 m. mole) of amine representing 94% yield and having an optical rotation $[\alpha]_{578} = -63.8$ (C=1.11, CH₃OH). From the aqueous liquid remaining after extraction with chloroform, it was possible to recover 14.71 g. of dioxaphosphorinane after acidification, representing an 88% yield.

EXAMPLE 14

Separation of the optical isomers of methionine with (+)-1,3,2-dioxaphosphorinane, 5,5-dimethyl-4-(2'-chlorophenyl)-2-hydroxy-2-oxide (Compound 9 in Table 1).

A mixture of 7.64 g. (50.0 m. mole) of the racemate of methionine and 13.83 g. (50.0 m. mole) of the (+)-dioxaphosphorinane was dissolved with heating in a mixture of 70 ml. of 96% ethanol and 35 ml. of water. After cooling and allowing the solution to stand with agitation for 5 hours, the precipitated diastereomeric salt was sucked off, washed with water and dried. The production was 5.46 g. (12.8 m. mole) representing a 26% yield and having an optical rotation $[\alpha]_{578} = +33.3$. This salt was agitated for 4 hours with 45 ml. of water, 6 ml. of concentrated hydrochloric acid and 10 ml. of methanol. From the nondissolved fraction, it was possible to recover by filtration, washing with water and drying 3.42 g. (12.4 m. mole) of dioxaphosphorinane representing a 96% yield. The dissolved fraction was concentrated by evaporation, dissolved in water and purified over a Dowex −H+ column. After the purified product was concentrated by evaporation, 1.6 g. (10.7 m. mole) of (+)-methionine representing a yield of 84% were obtained having an optical rotation $[\alpha]_{578} = +21.8$ (C=0.797, 0.2N hydrochloric acid).

EXAMPLE 15

Separation of the optical isomers of 1,2-di(4'-chlorophenyl)-1,2-diamino-ethane by means of (−)-1,3,2-dioxaphosphorinane, 5,5-dimethyl-4-phenyl-2-hydroxy-2-oxide (Compound 1 in Table 1).

A mixture of 12.5 g. (44.6 m. mole) of the (−)-dioxaphosphorinane and 12.5 g. (44.5 m. mole) of the diamine was dissolved with heating in 75 ml. of 96% ethanol. The mixture was cooled by allowing it to stand for 5.5 hours with agitation and the occasional addition of seed crystals. The precipitate was filtered, washed with an ethanol/ether mixture and then with ether and subsequently dried. The production was 6.38 g. (12.2 m. mole) of diastereomeric salt representing a 27% yield and having an optical rotation $[\alpha]_{578} = +63.8$. The diastereomeric salt was agitated with 2 g. of sodium hydroxide in 50 ml. of water. 25 ml. of chloroform was added and the mixture was agitated for 0.5 hour. After dilution with 50 ml. of water and 25 ml. of chloroform, the layers were separated. The aqueous phase was extracted with 50 ml. of chloroform. The chloroform fractions were washed with water, dried and concentrated by evaporation. The resulting oil, which solidified on cooling, has an optical rotation $[\alpha]_{578} = +150.2$ and weighed 3.38 g. (12.0 m. mole) representing a 99% yield. The total production of dioxaphosphorinane was 9.46 g. representing an 88% yield.

While presently preferred embodiments of the invention have been described in particularity with reference to the examples, the invention may be otherwise embodied within the scope of the appended claims.

What is claimed is:

1. A dioxaphosphorinane of the general formula:

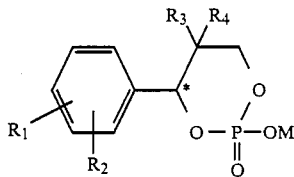

wherein, M represents a hydrogen atom, a metal ion or an ammonium ion; R1 and R2, individually, represents a hydrogen atom, a halogen atom, an alkyl group having from 1 to 4 carbon atoms, an alkoxy group having from 1 to 4 carbon atoms or a nitro group or, together, represent a methylene dioxy group; and R3 and R4, individually, represents a halogen atom, an alkyl group having from 1 to 4 carbon atoms or a hydrogen atom so long as only one of the grous R3 and R4 represents a hydrogen atom or, together, represent a cyclohexyl group.

2. A compound as described in claim 1 wherein R1 and R2, individually, represents a hydrogen atom, a chlorine atom, a methyl group, an ethyl group, a methoxy group, an ethoxy group or a nitro group or, together, represent a 3,4-methylene dioxy group; and R3 and R4, individually, represents a chlorine atom, a methyl group or a hydrogen atom so long as only one of the groups R3 and R4 represents a hydrogen atom or, together, represent a cyclohexyl group.

3. A compound as described in claim 1 wherein R1 represents a hydrogen atom or a halogen atom at the para-position, R2 represents a methoxy group or chlorine atom at the ortho-position and R3 and R4 represent methyl groups.

4. A dioxaphosphorinane as described in claim 1 wherein the isomers are optically active.

5. A dioxaphosphorinane as described in claim 2 wherein the isomers are optically active.

6. A dioxaphosphorinane as described in claim 3 wherein the isomers are optically active.

7. A method for preparing optically active isomers of dioxaphosphorinanes comprising:
   (a) reacting the corresponding racemate of one of the optically active dioxaphosphorinanes of the general formula:

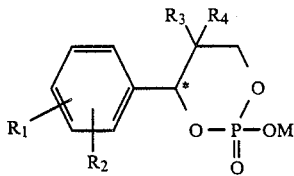

wherein, M represents a hydrogen atom, a metal ion or an ammonium ion; R1 and R2, individually, represents a hydrogen atom, a halogen atom, an alkyl group having from 1 to 4 carbon atoms, an alkoxy group having from 1 to 4 carbon atoms or a nitro group or, together, represent a methylene dioxy group; and R3 and R4, individually, represents a halogen atom, an alkyl group having from 1 to 4 carbon atoms or a hydrogen atom so long as only one of the groups R3 and R4 represents a hydrogen atom or, together, represent a cyclohexyl group, in a solvent with an optically active amino-compound to form a diastereomeric salt which at least partially crystallizes out and a diastereomeric salt which remains in solution;

(b) separating the crystallized-out salts from the dissolved salts; and (c) hydrolyzing one or both of the separated salts.

8. The method as described in claim 7 wherein the corresponding racemate which is reacted is one of the optically active dioxaphosphorinanes wherein R1 and R2, individually, represents a hydrogen atom, a chlorine atom, a methyl group, an ethyl group, a methoxy group, an ethoxy group or a nitro group or, together, represent a 3,4-methylene dioxy group; and R3 and R4, individually, represents a chlorine atom, a methyl group or a hydrogen atom so long as only one of the groups R3 and R4 represents a hydrogen atom or, together, represent a cyclohexyl group.

9. The method as described in claim 7 wherein the corresponding racemate which is reacted is one of the optically active dioxaphosphorinanes wherein R1 represents a hydrogen atom or a halogen atom at the para-position, R2 represents a methoxy group or chlorine atom at the ortho-position and R3 and R4 represent methyl groups.

10. A method for preparing optically active isomers of dioxaphosphorinanes comprising:

(a) reacting the corresponding racemate of one of the optically active dioxaphosphorinanes of the general formula:

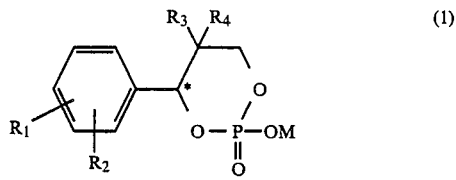

(1)

wherein, M represents a hydrogen atom, a metal ion or an ammonium ion; R1 and R2, individually, represents a hydrogen atom, a halogen atom, an alkyl group having from 1 to 4 carbon atoms, an alkoxy group having 1 to 4 carbon atoms or a nitro group or, together, represent a methylene dioxy group; and R3 and R4, individually, represents a halogen atom, an alkyl group having from 1 to 4 carbon atoms or a hydrogen atom so long as only one of the groups R3 and R4 represents a hydrogen atom or, together, represent a cyclohexyl group, in a solvent with an optically active amino-compound selected from the group consisting of (−)-ephedrine, (+)-2-amino-1-phenyl-1,3-propanediol, (−)-2-amino-1-butanol and (−)-para-hydroxyphenylglycine to form a diastereomeric salt which at least partially crystallizes out and a diastereomeric salt which remains in solution;

(b) separating the crystallized-out salts from the dissolved salts; and (c) hydrolyzing one or both of the separated salts.

11. The method as described in claim 10 wherein the corresponding racemate which is reacted is one of the optically active dioxaphosphorinanes wherein R1 and R2, individually, represents a hydrogen atom, a chlorine atom, a methyl group, an ethyl group, a methoxy group, an ethoxy group or a nitro group or, together, represent a 3,4-methylene dioxy group; and R3 and R4, individually, represents a chlorine atom, a methyl group or a hydrogen atom so long as only one of the groups R3 and R4 represents a hydrogen atom or, together, represent a cyclohexyl group.

12. The method as described in claim 10 wherein the corresponding racemate which is reacted is one of the optically active dioxaphosphorinanes wherein R1 represents a hydrogen atom or a halogen atom at the para-position, R2 represents a methoxy group or chlorine atom at the ortho-position and R3 and R4 represent methyl groups.

13. A method for separating an optically active isomer of an amino-compound from its corresponding racemate using a dioxaphosphorinane comprising:

(a) reacting the racemate with an optically active dioxaphosphorinane of the general formula:

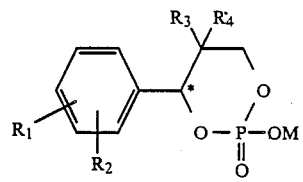

wherein, M represents a hydrogen atom, a metal ion or an ammonium ion; R1 and R2, individually, represents a hydrogen atom, a halogen atom, an alkyl group having from 1 to 4 carbon atoms, an alkoxy group having from 1 to 4 carbon atoms or a nitro group or, together, represent a methylene dioxy group; and R3 and R4, individually, represents a halogen atom, an alkyl group having from 1 to 4 carbon atoms or a hydrogen atom so long as only one of the groups R3 and R4 represents a hydrogen atom or, together, represent a cyclohexyl group, to form a diasteromeric salt which crystallizes out and a diasteromeric salt which remains in solution and (b) separating the two salts from one another.

14. The method as described in claim 13 using an optically active dioxaphosphorinane wherein R1 and R2, individually, represents a hydrogen atom, a chlorine atom, a methyl group, an ethyl group, a methoxy group, an ethoxy group or a nitro group or, together, represent a 3,4-methylene dioxy group; and R3 and R4, individually, represents a chlorine atom, a methyl group or a hydrogen atom so long as only one of the groups R3 and R4 represents a hydrogen atom or, together, represent a cyclohexyl group.

15. The method as described in claim 13 using an optically active dioxaphosphorinane wherein R1 represents a hydrogen atom or a halogen atom at the para-position, R2 represents a methoxy group or chlorine atom at the ortho-position and R3 and R4 represent methyl groups.

16. The method as described in claim 13 wherein the separated salts are hydrolyzed.

17. The method as described in claim 14 wherein the separated salts are hydrolyzed.

18. The method as described in claim 15 wherein the separated salts are hydrolyzed.

19. The method as described in claim 15 wherein the amino-compound is para-hydroxyphenylglycine, phenylalanine, 1-phenyl-2-paramethoxyphenyl-ethylamine, S-(amino-iminomethyl)-β-mercaptobutyric acid, N-[1-(4′-methoxyphenyl)-isopropyl]-N-ethylamine, 1,2,3,4-tetrahydro-5-methoxy-N-propyl-2-naphthalene-amine, 1,2-di-(4′-chlorophenyl)-1,2-diaminoethane, and methionine.

20. The method as described in claim 18 wherein the amino-compound is para-hydroxyphenylglycine, phenylalanine, 1-phenyl-2-paramethoxyphenyl-ethylamine, S-(amino-iminomethyl)-β-mercaptobutyric acid, N-[1-(4′-methoxyphenyl)-isopropyl]-N-ethylamine, 1,2,3,4-tetrahydro-5-methoxy-N-propyl-2-naphthalene-amine, 1,2-di(4′-chlorophenyl)-1,2-diaminoethane, and methionine.

* * * * *